United States Patent [19]

Harandi

[11] Patent Number: 5,146,032
[45] Date of Patent: Sep. 8, 1992

[54] INTEGRATED PROCESS FOR CONVERTING METHANOL TO GASOLINE AND DISTILLATES

[75] Inventor: Mohsen N. Harandi, Lawrenceville, N.J.

[73] Assignee: Mobil Oil Corporation, Fairfax, Va.

[21] Appl. No.: 806,780

[22] Filed: Dec. 12, 1991

Related U.S. Application Data

[63] Continuation of Ser. No. 658,491, Feb. 21, 1991, abandoned, which is a continuation-in-part of Ser. No. 601,955, Oct. 23, 1990, abandoned.

[51] Int. Cl.$^5$ .............................................. C07C 1/20
[52] U.S. Cl. ............................. 585/640; 585/329; 585/313; 585/469; 585/722; 585/312; 585/315; 585/316
[58] Field of Search .............. 585/329, 330, 413, 517, 585/518, 533, 469, 717, 640, 722, 312, 315, 316

[56] References Cited

U.S. PATENT DOCUMENTS

| | | | |
|---|---|---|---|
| 4,590,320 | 5/1986 | Sapre | 585/324 |
| 4,628,135 | 12/1986 | Owen et al. | 585/331 |
| 4,654,453 | 3/1987 | Tabak | 585/303 |
| 4,684,757 | 8/1987 | Avidan et al. | 585/331 |
| 4,746,761 | 5/1988 | Avidan et al. | 585/331 |
| 4,788,365 | 11/1988 | Harandi et al. | 585/312 |
| 4,935,568 | 6/1990 | Harandi et al. | 585/316 |
| 4,992,611 | 2/1991 | Morrison | 585/640 |

Primary Examiner—Asok Pal
Attorney, Agent, or Firm—Alexander J. McKillop; Charles J. Speciale; L. G. Wise

[57] ABSTRACT

An integrated process comprising the steps of pressurizing a $C_3^+$ olefin hydrocarbon stream and a methanol feed and contacting the $C_3^+$ hydrocarbon stream and methanol feed in a first reaction zone with a medium-pore shape selective oligomerization zeolite catalyst at elevated pressure and moderate temperature to convert at least a portion of the $C_3^+$ hydrocarbons and methanol feed to heavier liquid hydrocarbon product stream comprising olefinic gasoline and distillate range liquids. An ethene stream and a stream containing unreacted methanol and water are recovered from the first reaction zone effluent and the methanol is separated from the water.

The ethene and the separated unreacted methanol are contacted with a medium-pore shape selective zeolite catalyst in a second reaction zone at elevated temperature and moderate pressure to convert the methanol feed to hydrocarbons comprising $C_3^+$ olefins and cooling effluent from the second reaction zone to recover a $C_3^+$ olefin hydrocarbon stream and a $C_2^-$ light gas stream. The $C_3^+$ olefin hydrocarbon stream is fed to the first reaction zone with the methanol feed.

21 Claims, 1 Drawing Sheet

INTEGRATED PROCESS FOR CONVERTING METHANOL TO GASOLINE AND DISTILLATES

RELATED APPLICATIONS

This is a continuation of copending application Ser. No. 07/658,491 filed Feb. 21, 1991, which is a continuation-in-part of applicant's prior application Ser. No. 07/601,955, filed Oct. 23, 1990., now both abandoned.

BRIEF DESCRIPTION OF THE INVENTION

The present invention relates to a process for the conversion of oxygenates, such as methanol or dimethyl ether (DME), to liquid hydrocarbons. The oxygenate feed is fed together with a light olefinic stream at elevated pressure and moderate temperature to a first reactor and contacted with an oligomerization zeolite catalyst to produce heavier liquid hydrocarbons.

The present invention is particularly directed to a process for the conversion of methanol feed and olefin hydrocarbons to gasoline and distillate range liquid hydrocarbons at elevated pressure and moderate temperature.

The present invention is more particularly directed to a process for the conversion of methanol and $C_3^+$ olefin hydrocarbons to gasoline and distillate range liquid hydrocarbons which comprises contacting the methanol and $C_3^+$ olefin hydrocarbons in a first reaction zone with a medium-pore shape selective oligomerization zeolite catalyst at elevated pressure and moderate temperature to convert at least a portion of the $C_3^+$ hydrocarbons and methanol feed to heavier liquid hydrocarbon product stream comprising olefinic gasoline and distillate range liquids.

The present invention also directed to a MTO/MOGD process in which a methanol feed and olefin hydrocarbons are fed to the MOGD reactor at elevated pressure and moderate temperature to convert the methanol feed and olefin hydrocarbon feed to olefinic gasoline and distillate range liquids.

The methanol feed that is not converted to olefins in the MOGD reactor, i.e. the unreacted methanol, is extracted from the MOGD effluent by water wash, optionally dewatered and then fed to the MTO reactor. An ethene containing stream is separated from the MOGD reactor effluent and can be optionally fed to the MTO reactor with the separated unreacted methanol at elevated temperature and moderate pressure to convert the ethene and separated unreacted methanol to $C_3^+$ olefin hydrocarbons. The $C_3^+$ olefin hydrocarbons are fed to the MOGD reactor with the original methanol feed.

BACKGROUND

In order to provide an adequate supply of liquid hydrocarbons for use as synfuels or chemical feedstocks, various processes have been developed for converting coal and natural gas to gasoline, distillate and lubricants. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for increasing the yield of gasoline and diesel fuel by multi-stage techniques.

Recent developments in zeolite catalysts and hydrocarbon conversion processes have created interest in utilizing olefinic feedstocks for producing $C_5^+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2$-$C_5$ alkenes. This process may supplant conventional alkylation units. In Plank, Rosinski and Givens U.S. Pat. No(s). 3,960,978, and 4,021,502, disclose conversion of $C_2$-$C_5$ olefins alone or in admixture with paraffinic components, into higher hydrocarbons over crystalline zeolites having controlled acidity. Garwood et al have also contributed improved processing techniques to the MOGD system, as in U.S. Pat. No(s). 4,150,062, 4,211,640 and 4,227,992. The above-identified disclosures are incorporated herein by reference.

Conversion of lower olefins, especially propene and butenes, over ZSM-5 is effective at moderately elevated temperatures and pressures. The conversion products are sought as liquid fuels, especially the $C_5^+$ aliphatic and aromatic hydrocarbons. Olefinic gasoline is produced in good yield by the MOGD process and may be recovered as a product or recycled to the reactor system for further conversion to distillate-range products. Operating details for typical MOGD units are disclosed in Owen et al U.S. Pat. No(s). 4,445,031 and 4,456,779, and Tabak U.S. Pat. No. 4,433,185, incorporated herein by reference.

In addition to their use as shape selective oligomerization catalysts, the medium pore ZSM-5 type catalysts are useful for converting methanol and other lower aliphatic alcohols or corresponding ethers to olefins. Particular interest has been directed to a catalytic process ("MTO") for converting low cost methanol to valuable hydrocarbons rich in ethene and $C_3^+$ alkenes. Various processes are described in Batter et al U.S. Pat. No. 3,894,107, Chang et al U.S. Pat. No. 3,928,483, Lago U.S. Pat. No. 4,025,571, Daviduk et al U.S. Pat. No. 4,423,274, and Young U.S. Pat. No. 4,433,189, incorporated herein by "reference. It is generally known that the MTO process can be optimized to produce a major fraction of $C_2$-$C_4$ olefins. "Prior process proposals have included a separation section to recover ethene and other gases from by-product water and $C_5^+$ hydrocarbon liquids. The oligomerization process conditions which favor the production of $C_{10}$-$C_{20}$ and higher aliphatics tend to convert only a small portion of ethene as compared to $C_3^+$ olefins.

The Gould et al U.S. Pat. No. 4,579,999 discloses an integrated process for the conversion of methanol to gasoline and distillate. In a primary catalytic stage (MTO) methanol is contacted with zeolite catalyst to produce $C_2$-$C_4$ olefins and $C_5^+$ hydrocarbons. In a secondary catalytic stage (MOGD) containing an oligomerization catalyst comprising medium pore shape selective acidic zeolite at increased pressure, a $C_3^+$ olefins stream from the primary stage is converted to gasoline and/or distillate liquids.

The Harandi et al U.S. Pat. No. 4,899,002 discloses a process for the increased production of olefinic gasoline, which comprises the integration of oxygenates to olefin (MTO) conversion with olefin to gasoline conversion under moderate severity conditions. The product of the olefins to gasoline conversion is passed to an olefin to gasoline and distillate (MOGD) conversion zone for distillate production.

The methanol to olefin process (MTO) operates at high temperature and moderate pressure and high catalyst contact time in order to obtain efficient conversion of the methanol to olefins. These process conditions, however, produce an undesirable amount of aromatics and $C_2^-$ light gas stream and require a large investment in plant equipment.

The olefins to gasoline and distillate process (MOGD) operates at moderate temperatures and elevated pressures to produce olefinic gasoline and distillate products. When the conventional MTO process effluent is used as a feed to the MOGD process, the aromatic hydrocarbons produced in the MTO unit are desirably separated and a relatively large volume of MTO product effluent has to be cooled and treated to separate a $C_2^-$ light gas stream, which is unreactive, except for ethene which is reactive to only a small degree, in the MOGD reactor, and the remaining hydrocarbon stream has to be pressurized to the substantially higher pressure used in the MOGD reactor.

The problems to be solved were to reduce the overall size and investment in the MTO reactor, reduce the amount of the methanol feed fed to the MTO reactor in order that the process could be carried out under lower severity operating conditions which improves selectivity to not produce aromatics and not produce large amounts of $C_2^-$ light gas. At the same time it was desired to maintain the total effective amount of the methanol feed converted to olefins and to improve the overall selectivity of the MTO/MOGD process to produce more olefinic gasoline and distillates.

OBJECTS OF THE INVENTION

It is an object of the present invention to improve the overall operation and cost of conversion of methanol to gasoline and distillate by a process which comprises feeding the entire methanol feed to the MOGD reactor together with a light olefin hydrocarbon stream.

It is another object of the present invention to separate and recover unconverted methanol from the MOGD reactor effluent and to recycle a portion of the unconverted methanol to the MOGD reactor.

It is another object of the present invention to improve the overall operation and cost of conversion of methanol to gasoline and distillate by process integration of a methanol to olefin conversion process with an olefin to gasoline and distillate conversion process.

It is another object of the present invention to reduce the size and investment in the methanol to olefin conversion process by feeding the entire methanol feed to a methanol and olefin to gasoline or distillate conversion step (MOGD) and separating unreacted methanol and ethene, and feeding the unreacted methanol and ethene to the methanol to olefin conversion process (MTO).

SUMMARY OF THE INVENTION

In accordance with the present invention methanol, dimethyl ether (DME) or other lower oxygenates containing less than four carbon atoms may be converted to liquid fuels particularly gasoline and distillate, in a continuous process with integration between major process units. The methanol feed, together with a light olefin hydrocarbon stream, e.g. a $C_3^+$ olefin hydrocarbon stream, is fed to an olefin to gasoline and distillate unit reactor (MOGD) to produce gasoline and distillate. Unreacted methanol is recovered from the MOGD reactor effluent and is recycled to the MOGD reactor or is fed to a methanol to olefins reactor (MTO) to produce olefin hydrocarbon feed to the MOGD reactor.

The present invention is specifically directed to an integrated process for the conversion of oxygenate feeds such as methanol and dimethyl ether to olefinic gasoline and distillate range liquid hydrocarbons. The process comprises the steps of pressurizing a $C_3^+$ olefin hydrocarbon stream and the methanol feed and contacting them in a first (MOGD) reactor with oligomerization catalyst at elevated pressure and moderate temperature to convert the $C_3^+$ olefin stream and methanol to a heavier liquid hydrocarbon stream comprising olefinic gasoline and distillate range hydrocarbons. The heavier liquid stream is cooled to preliminarily separate $C_3^+$ liquid hydrocarbons from $C_2^-$ light gas, unreacted methanol and by-product water. The $C_3^+$ liquid hydrocarbons can be further treated to recover an LPG stream, a $C_5$–$C_9$ olefinic gasoline stream and a $C_{10}$–$C_{20}$ distillate stream. The $C_{10}$–$C_{20}$ distillate stream can be hydrotreated to produce high quality distillate product.

The unreacted methanol is separated from the by-product water. The unreacted methanol, preferably along with the $C_2^-$ light gas, is contacted with zeolite catalyst in a second reactor (MTO) at elevated temperature and moderate pressure to convert the unreacted methanol to $C_3^+$ light olefin hydrocarbons. The effluent from the second reactor is cooled to separate a $C_3^+$ olefin hydrocarbon stream and a $C_2^-$ light gas stream. The $C_3^+$ hydrocarbon stream is fed with the original methanol feed to the first reactor as discussed above.

Advantageously, the first and second reactors can contain ZSM-5 type zeolite catalyst.

DETAILED DESCRIPTION OF THE INVENTION

Oxygenated Feed

Figure 1:
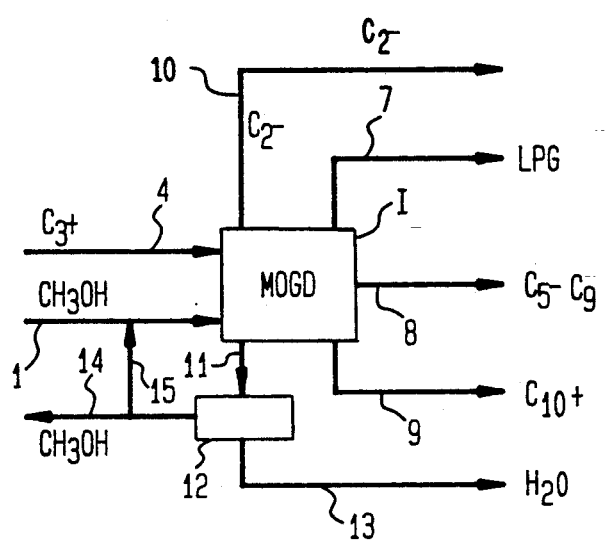
FIG. 1 is a process flow sheet showing the feeding of methanol feed and olefin hydrocarbons to the olefins to gasoline and distillate (MOGD) unit reactor and the process streams.

Numerous oxygenate organic compounds can be used as the feed to be converted to olefinic gasoline and distillate in the present invention. Since methanol or its ether derivative (DME) are industrial commodities from synthesis gas or the like processes, these materials are utilized in the description herein as preferred starting materials. It is understood by those skilled in the art that the methanol to olefin type processes can employ methanol, dimethyl ether and mixtures thereof, as well as other lower aliphatic alcohols and ethers, lower ketones and/or aldehydes. It is also understood by those skilled in the art to partially convert oxygenates, such as methanol, by dehydration, as in the catalytic reaction of methanol over gamma-alumina to produce DME intermediate. Typically, an equilibrium mixture ($CH_3OH \rightleftharpoons CH_3OCH_3 + H_2O$) is produced by partial dehydration. In the first reactor, methanol and olefins are converted to gasoline and distillate (MOGD); and in the second reactor, unreacted methanol from the first reactor and olefins are converted to lower olefins (MTO).

Catalyst

Catalyst versatility permits the same zeolite catalyst to be used in the first reactor unit oligomerization stage (MOGD) and in the second reactor unit methanol to olefins stage (MTO). While it is within the inventive concept to employ substantially different catalysts in these reactors, it is advantageous to employ a standard ZSM-5 catalyst having a silica to alumina molar ratio of 70:1 in the first and second reactors.

Recent developments in zeolite technology have provided a group of medium-pore shape-selective siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium-pore zeolites are favored for acid catalysis; however, the advantages of ZSM-5 structures may be utilized by employing highly siliceous material or crystalline metallosilicate having one or more tetrahedral species having varying degrees of acidity. ZSM-5 crystalline structure is readily recognized by its X-ray diffraction pattern, which is described in Argauer et al U.S. Pat. No. 3,702,866, incorporated by reference.

The zeolite catalysts preferred for use herein include the medium-pore (i.e., about 5-7 A) shape-selective crystalline aluminosilicate zeolites having a silica-to-alumina ratio of at least 12, a constraint index of about 1 to 12 and acid cracking activity of about 1-200. In an operating reactor the coked catalyst may have an apparent activity (alpha value) of about 1 to 80 under the process conditions to achieve the required degree of reaction severity. Representative of the ZSM-5 zeolites are ZSM-5, ZSM-11, ZSM-12, ZSM-22, ZSM-23, ZSM-35, ZSM-38, ZSM-48 and MCM-22. ZSM-5 is disclosed in U.S. Pat. No. 3,702,886 and U.S. Pat. Re. No. 29,948. The ZSM-5, ZSM-12, ZSM-22, ZSM-23, ZSM-35, ZSM-48 and MCM-22 catalyst are preferred. The MCM-22 catalyst is described in U.S. Pat. No. 4,954,325. Other suitable zeolites are disclosed in U.S. Pat. No(s). 3,709,979, 3,832,449, 4,076,979, 3,832,449, 4,076,842, 4,016,245, and 4,046,839, 4,414,423, 4,417,086, 4,517,396, and 4,542,251. The disclosures of the above mentioned patents are incorporated herein by reference. While suitable zeolites having a coordinated silica to metal oxide molar ratio of 20:1 to 200:1 or higher may be used, it is advantageous to employ a standard ZSM-5 having a silica to alumina molar ratio of about 25:1 to 70:1. A typical zeolite catalyst component having Bronsted acid sites may consist essentially of aluminosilicate ZSM-5 zeolite with 5 to 95 wt. % silica and/or alumina binder.

Certain of the ZSM-5 type medium pore shape-selective catalysts are sometimes known as pentasils. In addition to the preferred aluminosilicates, the borosilicate, ferrosilicate and "silicalite" materials may be employed. It is advantageous to employ a standard ZSM-5 having a silica:alumina molar ratio of 25:1 to 70:1 with an apparent alpha value of 1-80.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred. The zeolite catalyst crystals are normally bound with a suitable inorganic oxide, such as silica, alumina, etc. to provide a zeolite concentration of about 5 to 95 wt. %. A preferred catalyst comprises 25% to 65% H-ZSM-5 catalyst contained within a silica-alumina matrix binder and having a fresh alpha value of less than 600.

When employing a ZSM-5 type zeolite catalyst in a fluidized bed as a fine powder such a catalyst should comprise the zeolite suitably bound or impregnated on a suitable support with a solid density (weight of a representative individual particle divided by its apparent "outside" volume) in the range from 0.6-2 g/cc, preferably 0.9-0.6 g/cc. The catalyst particles can be in a wide range of particle sizes up to about 250 microns, with an average particle size between 20 and 100 microns, preferabaly in the range of 10-150 microns and with the average particle size between 40 and 80 microns. When these solid particles are placed in a reactor bed where the superficial fluid velocity is 0.3-2 ft./sec., fluidized bed operation is obtained. The velocity specified here is for an operation at a total reactor pressure of about 0 to 30 psig (100 to 300 kPa). Those skilled in the art will appreciate that at higher pressures, a lower gas velocity may be employed to ensure proper fluidized bed operation.

In the fluidized bed embodiments of the present invention it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt. % of the total catalyst in the reaction zone in the size range less than 32 microns. This class of fluidizable particles is classified as Geldart Group A.

The light olefin production is promoted by the zeolite catalysts having a high concentration of Bronsted acid reaction sites. Accordingly, an important criterion is selecting and maintaining the catalyst to provide either fresh catalyst having acid activity or by controlling catalyst deactivation and regeneration rates to provide an apparent average alpha value of about 1 to 50, preferably 1 to 10.

A further description of the zeolite catalyst is found in Owen et al U.S. Pat. No. 4,456,779 which is incorporated herein by reference.

The oligomerization catalysts preferred for use herein in the MOGD fixed bed reactor include the crystalline aluminosilicate zeolites having a silica to alumina ratio of at least 12, a constraint index of about 1 to 12 and acid cracking activity of about 160-200. A suitable catalyst for fixed bed operation is 65 wt. % HZSM-5 zeolite with an alumina binder in the form of cylindrical extrudates of about 1-5 mm. Other catalysts and processes suitable for converting methanol/DME to lower olefins are disclosed in Bonafaz U.S. Pat. No. 4,393,265, Vogt et al U.S. Pat. No. 4,387,263, and Marosi et al European Patent Application No. 0081683.

The ZSM-5 type catalysts are particularly advantageous for use in the present invention because the same material may be employed for dehydration of methanol to DME, conversion of methanol to lower olefins and oligomerization reactions. A particular advantage of the process of the present invention is that the spent catalyst from a higher pressure unit can be used in a lower pressure unit as fresh make-up catalyst.

REACTORS

A number of different types of reactors can be used in the above mentioned processes including tubular, moving bed, fixed bed, fluid bed and riser reactors. The preferred reactor types and the operations of each in the processes are briefly described below.

MOGD Reactor I

The MOGD reaction is preferably carried out in a fixed bed multi-stage reactor. Suitable reactor designs, process conditions and techniques are described in Harandi et al U.S. Pat. No(s). 4,777,316, and 4,877,921, Gould U.S. Pat. No. 4,579,999, and Owen et al U.S. Pat. No. 4,456,779, all of which are incorporated herein by reference thereto.

Though a fixed bed multi-stage reactor is preferred for the MOGD reaction system, in certain circumstances a fluidized bed reactor system can be used. For example, see Harandi et al U.S. Pat. No. 4,877,921 which is incorporated herein by reference thereto.

MTO Reactor II

The MTO reaction is preferably carried out in a fluidized bed reactor because of the highly exothermic nature of the methanol to olefin reaction. In a preferred MTO reactor, a bed of finely divided (<150 microns) ZSM-5 catalyst is maintained in a turbulent fluidization regime. Hot feedstock vapor is passed upwardly through the fluidized bed at a superficial velocity of about 0.3 to 2 meters per second, maintaining a bed density of about 200 to 600 kg/m$^3$. By operating at about 520° C.±20° C. and a catalyst activity sufficient to yield a propane:propene ratio of about 0.02 to 0.3:1, the production of ethylene and $C_3^-$ paraffins can be controlled at a low level.

A suitable reactor and operating technique for carrying out this step of the invention are disclosed in Gould et al Ser. No. 687,045, filed Dec. 28, 1984. Other fluidized bed reactor systems suitable for use in the MTO reactor stage are disclosed in Avidan U.S. Pat. No. 4,746,762 and Harandi et al U.S. Pat. No. 4,777,316, both of which are incorporated herein by reference.

Though fluidized bed reactors are preferred for the MTO reactor stage, multi-stage fixed bed reactors provided with inter-stage cooling can also be used. See, for example, Graziani et al U.S. Pat. No. 4,542,252.

In the description used in the present application, metric units and parts by weight are employed unless otherwise stated. Various reactor configurations ,au be used, including fluidized bed catalytic reactors, moving bed and multi-stage fixed bed reactors.

The invention is further described with reference to the figures of the drawings.

DESCRIPTION OF THE FIGURES OF THE DRAWINGS

Referring to FIG. 1 methanol feed in line 1 is fed to the MOGD reactor I to selectively produce distillate hydrocarbons. The methanol feed can contain 0 to 50% by weight water, generally 5 to 40% by weight water, typically 4 to 20% by weight water. Preferably the methanol feed contains less than 5% by weight water. A $C_3^+$ olefin hydrocarbon feed, which is typically derived from a thermal or catalytic cracking operation, is fed through line 4 to the MOGD reactor I.

The methanol feed fed through line 1 and $C_3^+$ olefin feed fed through line 4 are contacted in reactor I with HZSM-5 catalyst where the methanol is converted to lower olefins, gasoline, distillate, and by-product water. The water is formed by the dehydration of the methanol.

The $C_3^+$ olefin hydrocarbon feed fed through line 4 can have the following composition.

|  | Wt. % | Typically Wt. % |
|---|---|---|
| $C_2^-$ | 0–14 | 0–5 |
| $C_3$–$C_4$ | 0–100 | 90–99 |
| $C_5$–$C_9$ | 100–0 | 0–5 |
| $C_{10}$–$C_{20}$ | 0–5 | 0 |

The $C_2^-$ stream and the $C_{10}$–$C_{20}$ stream are normally removed prior to feeding the stream to the MOGD reactor.

A suitable $C_3^+$ olefin feed stream can be obtained from a dehydrogenation plant, e.g. dehydrogenation of a propane stream.

The methanol feed and the remaining $C_3^+$ olefin feed are fed to reactor I at 0.01 to 10 WHSV, preferably 0.1 to 5.0 WHSV and more preferably at 0.3 to 1.0 WHSV, based on olefins and methanol content of the feed. The mixed methanol and $C_3^+$ olefin hydrocarbon feed is contacted in reactor I with an HZSM-5 catalyst arranged in a multi-stage fixed bed reactor preferably having three to four stages. Prior to entering the reactor I the mixed feed is pressurized by means not shown to the elevated pressure of the reactor I.

The reactor I is operated to selectively produce distillate hydrocarbons at a temperature of 177 to 371° C. (350 to 700° F.), preferably 204 to 343° C. (400 to 65° F.) and more preferably 204 to 316° C. (400 to 600° F.). The reactor I is operated at a pressure of 4237 to 20,780 kPa (600 to 3000 psig), preferably 4237 to 10,440 kPa (600 to 1500 psig) and more preferably 5600 to 7000 kPa (800 to 1000 psig).

After separation of any unconverted methanol and water present, the reactor I hydrocarbon effluent has the following composition.

|  | Typically Wt. % |
|---|---|
| $C_2^-$ | 1–2 |
| $C_3$–$C_4$ | 8–12 |
| $C_5$–$C_9$ | 15–30 |
| $C_{10}$–$C_{20}$ | 60–75 |

The aromatics content of gasoline fraction is 0–12 wt. %, based on total converted hydrocarbons.

At least 50% and preferably at least 95% of the methanol feed is converted to hydrocarbons.

The reactor I effluent is separated by means not shown into a $C_2^-$ light gas stream withdrawn through line 10; a gas stream comprising $C_3$–$C_4$ (LPG) hydrocarbons withdrawn through line 7; a $C_5$–$C_9$ olefinic gasoline stream withdrawn through line 8; and a $C_{10}$–$C_{20}$ distillate hydrocarbon stream Withdrawn through line 9. The unreacted methanol and water present are separated by cooling, phase separation, and in some cases by water washing of the hydrocarbon effluent leaving reactor I, and are withdrawn through line 11 and are fed to methanol-water separator 12, which is preferably a distillation tower. The methanol is separated from the water. The water is withdrawn through line 13. The unreacted methanol is withdrawn through line 14. At least a portion of the unreacted methanol can be recycled through line 15 to the methanol line 1. The $C_2^-$ light gas comprises mostly ethane and ethene. It may also contain small amounts of methane and hydrogen.

In an embodiment of the present invention the methanol and water stream withdrawn from the MOGD reactor in line 11 is contacted with the $C_3^+$ olefin feed in line 4, by means not shown, to extract methanol from water. The $C_3^+$ olefin feed containing the extracted methanol is then fed to the MOGD reactor. This extraction step reduces the distillation requirement for the methanol-water separations. The higher pressures increase selectivity to distillate hydrocarbons. At any particular selected pressure the lower temperatures increase selectivity to distillate.

Figure 2:
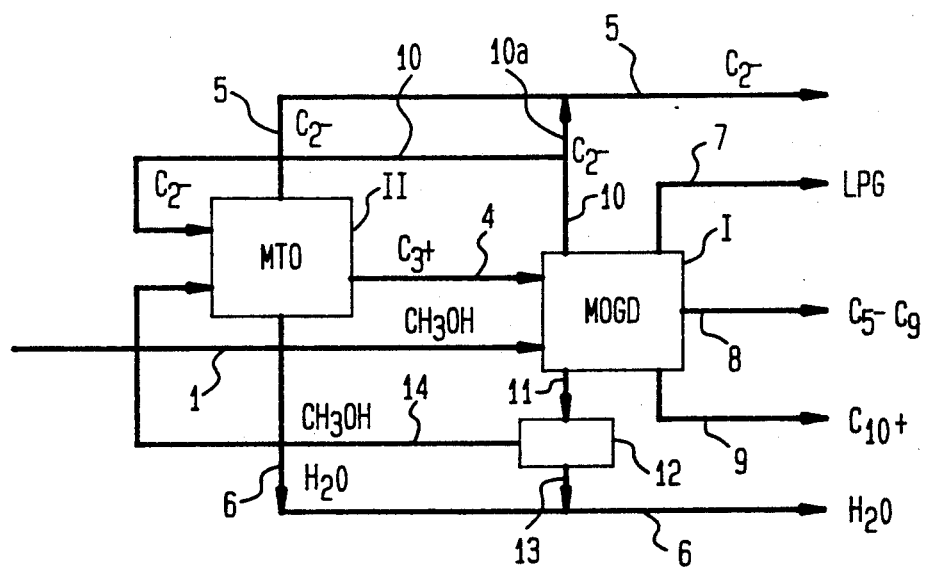
FIG. 2 is a process flow sheet showing the integration of the methanol to olefins (MTO) unit reactor and the olefins to gasoline and distillate (MOGD) unit reactor operations and the process streams.

Referring to FIG. 2, the methanol feed is fed through line 1 to the MOGD reactor I. The methanol feed can contain 0 to 50% by weight water, generally 5 to 40% by weight water, typically 4 to 20% by weight water. Preferably the methanol feed contains less than 5% by weight water. A $C_3^+$ olefin hydrocarbon feed is fed through line 4 to the MOGD reactor I. The $C_3^+$ olefin feed stream can be supplemented with $C_3^+$ hydrocarbons derived from a thermal or catalytic cracking operation. The process is described with reference to producing gasoline and distillate boiling range hydrocarbons.

The $C_3^+$ olefin containing stream and the methanol feed are fed through lines 4 and 1, respectively, to the MOGD reactor I. The $C_3^+$ olefin feed and the methanol can be mixed before entering the reactor or after they enter the reactor. The methanol and the $C_3^+$ olefin are fed to reactor I at 0.01 to 10 WHSV, preferably 0.1 to 5.0 WHSV and more preferably 0.3 to 1.0 WHSV, based on olefins plus methanol. The mixed methanol and $C_3^+$ olefin hydrocarbon feed is contacted in reactor I with an HZSM-5 catalyst arranged in a multi-stage fixed bed reactor preferably having three or four stages. Prior to entering the reactor I the feed is pressurized by means not shown to the substantially elevated pressure of the reactor I.

The reactor I is operated at a temperature of 177 to 371° C. (350 to 700° F.), preferably 204 to 343° C. (400 to 650° F.) and more preferably 204 to 316° C. (400 to 600° F.) The reactor I is operated at a pressure of 5237 to 20,780 kPa (600 to 3000 psig), preferably 4237 to 10,440 kPa (600 to 1500 psig) and more preferably 5600 to 7000 kPa (800 to 1000 psig). At the lower pressures gasoline products are selectively produced, while at the higher pressures lubricating oil stocks are selectively produced.

After separation of unconverted methanol and water, the reactor I hydrocarbon effluent has the following composition.

|  | Typically Wt. % |
| --- | --- |
| $C_2^-$ | 1-2 |
| $C_3-C_4$ | 8-12 |
| $C_5-C_9$ | 15-30 |
| $C_{10}-C_{20}$ | 60-75 |

Aromatics content of gasoline fraction is 0-12 wt. %, based on total hydrocarbons.

At least 50% and preferably at least 95% of the methanol feed is converted to olefin hydrocarbons.

The reactor I effluent is separated by means not shown into a $C_2^-$ light gas stream withdrawn through line 10 which is fed to reactor II or removed from the system through lines 10a and 5; a gas stream comprising $C_3-C_4$ (LPG) hydrocarbons withdrawn through line 7; a $C_5-C_9$ olefinic gasoline stream withdrawn through line 8; and a $C_{10}-C_{20}$ distillate hydrocarbon stream withdrawn through line 9. The unreacted methanol and water are separated by cooling and phase separation and are withdrawn through line 11 and are fed to methanol-water separator 12. The recovered unreacted methanol is separated from the water. The water is withdrawn through line 13 and line 6. The unreacted methanol is withdrawn through line 14 and fed to the MTO reactor II. Unreacted methanol may also be recovered by water washing the MOGD hydrocarbon effluent stream by means not shown and the methanol fed to the MTO reactor II.

The separated unreacted methanol in line 14, preferably together with the separated $C_2^-$ light gas stream withdrawn from the MOGD reactor I, is fed to reactor II and contacted with HZSM-5 catalyst. The methanol is converted to lower olefins and gasoline and by-product water. The olefin content of the $C_2^-$ light gas can also be upgraded to heavier hydrocarbons in the MTO reactor II.

The unreacted methanol in line 14 is fed to reactor II at 0.2 to 200 WHSV, preferably 0.3 to 3 WHSV and more preferably 0.5 to 2 WHSV. The reactor II is operated preferably as a dense fluidized bed at elevated temperatures of 260 to 538° C. (500 to 1000° F.), preferably 427 to 510° C. (800 to 950° F.), and more preferably 471 to 504° C. (880 to 940° F.). The reactor II is operated at moderate pressures of 101 to 789 kPa (0 to 100 psig), preferably 170 to 652 kPa (10 to 80 psig), and more preferably 239 to 308 kPa (20 to 30 psig). The reactor II effluent is cooled by means not shown and the by-product water is recovered by phase separation and withdrawn through line 6. After separation of water, the reactor II hydrocarbon effluent has the following composition.

|  | Typically Wt. % |
| --- | --- |
| $C_2^-$ | 10-14 |
| $C_3-C_4$ | 45-55 |
| $C_5-C_9$ | 25-35 |
| $C_{10}-C_{20}$ | 0-5 |

Aromatics content of gasoline fraction is typically 10-14 wt. %, based on total hydrocarbons.

At least 70% and preferably at least 99.9% of the methanol feed is converted to olefin hydrocarbons.

The effluent hydrocarbons are treated to separate an overhead $C_2^-$ light gas stream which is withdrawn through line 5 and a liquid $C_3^+$ olefin hydrocarbon stream which is withdrawn through line 4.

The $C_3^+$ olefin hydrocarbon stream withdrawn through line 4 and the methanol feed in line 1 are fed to the MOGD reactor I as described above.

Water and methanol present in the MOGD reactor effluent are separated and withdrawn through line 11 and fed to methanol-water separator 12. The methanol is separated from the water. The water is withdrawn through line 13. The unreacted methanol is withdrawn though line 14. The unreacted methanol is fed through line 14 to MTO reactor II and the water is withdrawn through line 6. In the event there is any appreciable amount of unreacted methanol present in streams 7 and/or 8, the streams can be washed with water to eliminate methanol in these streams and the recovered methanol can be fed to reactor II.

At the higher pressures a substantial amount of $C_{20}^+$ hydrocarbons are obtained which can be hydrotreated and used as lubricant stock. The relative proportion of $C_5$-$C_9$ gasoline and $C_{10}$-$C_{20}$ distillate is determined by the reaction conditions in reactor I and the recycle rate of the $C_5$-$C_9$ hydrocarbon fraction. The higher temperatures and lower pressures favor the $C_5$-$C_9$ gasoline production and the lower temperatures, higher pressures and $C_5$-$C_9$ gasoline recycle favor heavy $C_{10}$-$C_{20}$ distillate production. The $C_5$-$C_9$ gasoline fraction withdrawn through line 8 can optionally be recycled by means not shown to the MOGD reactor I to increase the production of distillate.

The lower pressures increase the selectivity to gasoline hydrocarbons, while the higher pressures increase selectivity to distillate hydrocarbons.

At any particular selected pressure the higher temperatures, for example 371 to 538° C. (700 to 1000° F.), preferably 371 to 482° C. (700 to 900° F.) and more preferably 371 to 427° C. (700 to 800° F.), increase selectivity to gasoline, while the lower temperatures 260 to 371° C. (500 to 700° F.), preferably 288 to 343° C. (550 to 650° F.), and more preferably 316 to 343° C. (600 to 650° F.), increase selectivity to distillate.

The MOGD reactor I can be operated at a temperature of 177 to 538° C. (350 to 1000° F.), preferably 204 to 482° C. (400 to 800° F.), and more preferably 204 to 371° C. (400 to 700° F.). The MOGD reactor I can be operated at a pressure of 308 to 20,780 kPa (30 to 3000 psig), preferably 308 to 10,440 kPa (30 to 1500 psig), and more preferably 308 to 7000 kPa (30 to 1000 psig).

MOGD Gasoline Mode

When the process is carried out to selectively produce gasoline boiling range hydrocarbons the methanol feed, and the $C_3^+$ olefin hydrocarbon feed from MTO reactor II are fed to the MOGD reactor I at 0.01 to 100 WHSV, preferably 0.1 to 5.0 WHSV and more preferably 0.3 to 1.0 WHSV. The mixed methanol and $C_3^+$ olefin hydrocarbon feed is contacted in reactor I as before with an HZSM-5 catalyst arranged in a multi-stage fixed bed reactor.

The reactor I is operated at a temperature of 260 to 583° C. (500 to 1000° F.), preferably 343 to 482° C. (650 to 800° F.), and more preferably 343 to 371° C. (650 to 700° F.). The reactor I is operated at a pressure of 308 to 10,440 kPa (30 to 1500 psig), preferably 308 to 5600 kPa (30 to 800 psig) and more preferably 308 to 4237 kPa (30 to 600 psig). At the conditions recited gasoline boiling range hydrocarbon products are selectively produced.

MOGD Distillate Mode

When the process is carried out to selectively produce distillate boiling range hydrocarbons, the $C_3^+$ olefin hydrocarbon feed from the MTO reactor II and the methanol feed are fed to the MOGD reactor I at 0.01 to 10 WHSV, preferably 0.1 to 5.0 WHSV and more preferably at 0.3 to 1.0 WHSV. The mixed methanol and $C_3^+$ olefin hydrocarbon feed is contacted in reactor I with an HZSM-5 catalyst arranged in a multi-stage fixed bed reactor.

The reactor I is operated at a temperature of 177 to 371° C. (350 to 700° F.), preferably 204 to 343° C. (400 to 650° F.) and more preferably 204 to 316° C. (400 to 600° F.). The reactor I is operated at a pressure of 4237 to 20,780 kPa (600 to 3000 psig), preferably 4237 to 10,440 kPa (600 to 1500 psig) and more preferably 5600 to 7000 kPa (800 to 1000 psig). At the conditions recited distillate range hydrocarbons are selectively produced.

The present invention is illustrated by the following Example.

EXAMPLE

This Example is described with reference to FIG. 1 of the drawings. The FIG. 1 is a schematic flow sheet of the process of the present invention. In this embodiment the process is carried out to selectively produce distillate hydrocarbons.

A $C_3^+$ olefin hydrocarbon stream having the following composition is fed through line 4.

|  | Wt. % |
|---|---|
| $C_2^-$ | 12 |
| $C_3$-$C_4$ | 52 |
| $C_5$-$C_9$ | 33 |
| $C_{10}$-$C_{20}$ | 3 |

The aromatic content of the gasoline fraction is 12 wt. %, based on total hydrocarbons.

Where the process is carried out to selectively produce distillate hydrocarbons, the $C_2^-$ light gas stream, the aromatic hydrocarbons and the $C_{10}$-$C_{20}$ hydrocarbons are preferably removed.

The MOGD reactor I is operated in the distillate mode. The pressure of the $C_3^+$ hydrocarbons is increased by pump means not shown to 5600 to 7000 kPa (800 to 1000 psig) and fed to separation means not shown. In the separation means an overhead $C_2^-$ light gas stream, a $C_5$-$C_9$ aromatics stream and a $C_{10}$-$C_{20}$ stream are removed. The remaining $C_3$-$C_4$ olefin hydrocarbons and $C_5$-$C_9$ hydrocarbons are then fed through line 4 to the MOGD reactor I. The pressure of the methanol feed is increased to 5600 to 7000 kPa (800 to 1 psig) by pump means not shown and fed through line 1 to the MOGD reactor I. The feed rate of the combined $C_3$-$C_4$ and $C_5$-$C_9$ hydrocarbon stream in line 4 and he methanol stream in line 1 to the MOGD reactor I is 0.3 to 1.0 WHSV. The reactor I feed includes a 3:1 weight ratio of recycle of the line 8 $C_5$-$C_9$ product stream by means not shown.

The methanol and $C_3$-$C_4$ and $C_5$-$C_9$ olefin hydrocarbons feed and recycle $C_5$-$C_9$ hydrocarbons are mixed in the reactor I and contacted with HZSM-5 catalyst in a multi-stage fixed bed reactor having three stages. The reactor I is operated under conditions to optimize distillate product at a pressure of 5600 to 7000 kPa (800 to 1000 psig) and at a temperature of 204 to 316° C. (400 to 600° F.). A portion or all of the $C_5$-$C_9$ fraction withdrawn through line 8 can be recycled to the MOGD reactor.

The reactor I effluent hydrocarbon product is withdrawn and separated into the desired process streams. Water and unconverted methanol are separated from the hydrocarbons and are withdrawn through line 11. The hydrocarbon portion of the MOGD reactor effluent typically has the following composition.

|  | Wt. % |
|---|---|
| $C_2^-$ | 1.0 |
| $C_3$-$C_4$ | 7.0 |
| $C_5$-$C_9$ | 29 |

| | Wt. % |
|---|---|
| $C_{10}-C_{20}$ | 63 |

The methanol conversion to hydrocarbons is about 70%.

The $C_2^-$ light gas in line 10 can be removed for ethene recovery. The MOGD effluent hydrocarbon stream is fractionated in a conventional manner with the $C_3C_4$ (LPG) being removed through line 7; the $C_5-C_9$ olefin gasoline being removed through line 8; and the $C_{10}-C_{20}$ distillate stream being removed through line 9. The unconverted methanol and water in line 11 are fed to separator 12 in which the methanol is separated from the water. The unconverted methanol can be recycled to the MOGD reactor.

The MTO reactor in the conventional MTO/MOGD process operates at higher temperatures than applicant's MOGD reactor. The higher temperature operation of the MTO reactor results in the conversion of a portion of the methanol feed to aromatic hydrocarbons and to $C_2^-$ light gas. In accordance with applicant's invention, in which all of the original methanol feed is fed to the MOGD reactor, the overall amounts of aromatic hydrocarbon and $C_2^-$ light gas products are significantly reduced.

Further, if applicant's entire methanol feed were fed to applicant's invention MTO reactor (FIG. 2), the size of MTO reactor and the investment needed for the MTO plant would be about three times as large.

The prior art process of feeding all of the methanol feed to the MTO reactor results in the production of more $C_2^-$ light gas and in the production of more aromatic hydrocarbons, both of which decrease the desired gasoline and heavy distillate production, respectively. In addition, an increased aromatics removal capacity is needed to remove the relatively larger amount of aromatics from the MTO effluent hydrocarbon product, since it is preferred not to have too large amount of aromatics the gasoline product and to not have any significant amount of aromatics in the heavy distillate product.

The foregoing description of the present invention has omitted various heating and cooling apparatus, catalyst regenerators, compressors and like equipment which are conventional and well known to those skilled in the art. Further, recycle streams other than those described can be utilized to optimize specifically desired process streams.

The described integrated processes provide effective means for converting oxygenated organic compounds such as methanol, DME, lower aliphatic ketones and aldehydes to valuable hydrocarbon products. Thermal integration is achieved by employing heating and cooling means between various process streams, towers, absorbers, etc., in a conventional manner.

Various modifications can be made to the systems, especially in the choice of equipment and non-critical processing steps. While the invention has been described by specific examples, there is no intent to limit the inventive concept except as set forth in the following claims.

What is claimed is:

1. An integrated process for converting an oxygenate feed to gasoline and distillate range liquid hydrocarbons comprising the steps of contacting the oxygenate feed, and at least a portion of a $C_3^+$ olefin hydrocarbon stream from a second reactor, in a first reactor with an oligomerization zeolite catalyst under oligomerization reaction conditions to convert the oxygenate feed and $C_3^+$ hydrocarbons to heavier hydrocarbons comprising olefinic gasoline and distillate range hydrocarbons, water containing unreacted oxygenated feed, and $C_2^-$ light hydrocarbons, separating a $C_2^-$ light hydrocarbon stream, separating hydrocarbons containing gasoline and distillate range liquid hydrocarbons from unreacted oxygenated feed and water, and separating the unreacted oxygenated feed from the water, and contacting the unreacted oxygenate feed and $C_2^-$ light hydrocarbons with a zeolite catalyst in a second reactor at elevated temperature of 500 to 1000° F. and moderate pressure of 0 to 100 psig to convert at least a portion of the unconverted oxygenate feed to $C_2^+$ olefin hydrocarbons and recovering an effluent comprising $C_2^-$ light hydrocarbons and $C_3^+$ olefin hydrocarbons and water, cooling the effluent from the second reactor and separating a $C_2^-$ olefin hydrocarbon stream, a $C_3^+$ olefin hydrocarbon stream and water, and feeding the $C_3^+$ olefin hydrocarbon stream to the first reactor.

2. The process of claim 1 wherein the oxygenated feed comprises methanol, dimethyl ether or mixtures thereof.

3. The process of claim 1 wherein the catalyst used in each of the first and second reactors comprises HZSM-5 catalyst.

4. The process of claim 1 to selectively produce distillate range hydrocarbons wherein the first reactor is operated at a temperature of 350 to 700° F. and a pressure of 600 to 3000 psig.

5. The process of claim 1 to selectively produce distillate range hydrocarbons wherein the first reactor is operated at a temperature of 400 to 650° F. and at a pressure of 600 to 1500 psig.

6. The process of claim 5 wherein the second reactor is operated at a temperature of 800 to 950° F. and at a pressure of 10 to 80 psig.

7. The process of claim 1 to selectively produce gasoline range hydrocarbons wherein the first reactor is operated at a temperature of 600 to 950° F. and pressure of 600 to 800 psig.

8. The process of claim 7 wherein the second reactor is operated at a temperature of 880 to 940° F. and pressure of 20 to 30 psig.

9. The process of claim 1 to selectively produce distillate range hydrocarbons wherein the first reactor zone is operated at a temperature of 500 to 650° F. and at a pressure of 700 to 1000 psig.

10. The process of claim 9 wherein the second reactor is operated at a temperature of 880 to 940° F. and a pressure of 20 to 30 psig.

11. The process of claim 1 wherein the effluent from the first reactor is cooled to separate hydrocarbons from unreacted methanol and water.

12. The process of claim 1 wherein the effluent from the first reactor is water washed to extract unreacted methanol.

13. The process of claim 1 wherein the unreacted methanol and water separated from the hydrocarbon effluent from the first reactor is contacted with the $C_3^+$ hydrocarbon effluent from the second reactor to extract methanol prior to the $C_3+$ hydrocarbon stream being fed to the first reactor.

14. The process of claim 1 wherein the effluent from the first reactor is water washed to extract unreacted methanol and the unreacted methanol is recycled to the first reactor.

15. An integrated process for converting an oxygenate feed comprising methanol, dimethylether or mixtures thereof to gasoline and distillate range liquid hydrocarbons comprising the steps of contacting the oxygenate feed, and at least a portion of a $C_3+$ olefin hydrocarbon stream from a second reactor, in a first reactor with an oligomerization zeolite catalyst under oligomerization reaction conditions to convert the oxygenate feed and $C_3+$ hydrocarbons to heavier hydrocarbons comprising olefinic gasoline and distillate range hydrocarbons, water containing unreacted oxygenated feed, and $C_2-$ light hydrocarbons, separating a $C_2-$ light hydrocarbon stream, separating hydrocarbons containing gasoline and distillate range liquid hydrocarbons from unreacted oxygenated feed and water, and separating the unreacted oxygenated feed from the water, and contacting the unreacted oxygenate feed in a second reactor at elevated temperature of 500 to 100° F. and moderate pressure of 0 to 100 psig to convert at least a portion of the unconverted oxygenate feed to $C_2+$ olefin hydrocarbons and recovering an effluent comprising $C_2-$ light hydrocarbons and $C_3+$ olefin hydrocarbons and water, cooling the effluent from the second reactor and separating a $C_2-$ olefin hydrocarbon stream, a $C_3+$ olefin hydrocarbon stream and water, and feeding the $C_3+$ olefin hydrocarbon stream to the first reactor.

16. The process of claim 15 wherein the catalyst used in each of the first and second reactors comprises HZSM-5 catalyst.

17. The process of claim 15 to selectively produce distillate range hydrocarbons wherein the first reactor is operated at a temperature of 400 to 650° F. and at a pressure of 600 to 1500 psig.

18. The process of claim 17 wherein the second reactor is operated at a temperature of 800 to 950° F. and at a pressure of 10 to 80 psig.

19. The process of claim 15 to selectively produce gasoline range hydrocarbons wherein the first reactor is operated at a temperature of 600 to 950° F. and pressure of 600 to 800 psig.

20. The process of claim 19 wherein the second reactor is operated at a temperature of 880 to 940° F. and pressure of 20 to 30 psig.

21. The process of claim 15 wherein the unreacted methanol and water separated from the hydrocarbon effluent from the first reactor is contacted with the $C_3+$ hydrocarbon effluent from the second reactor to extract methanol prior to the $C_3+$ hydrocarbon stream being fed to the first reactor.

* * * * *